United States Patent [19]

Kemp

[11] Patent Number: 4,967,016

[45] Date of Patent: Oct. 30, 1990

[54] ALKOXYLATION PROCESS CATALYZED BY BARIUM PHOSPHATE

[75] Inventor: Richard A. Kemp, Stafford, Tex.

[73] Assignee: Shell Oil Company, Houston, Tex.

[21] Appl. No.: 471,690

[22] Filed: Jan. 29, 1990

Related U.S. Application Data

[63] Continuation of Ser. No. 354,050, May 19, 1989, abandoned.

[51] Int. Cl.[5] ............................................. C07L 41/03
[52] U.S. Cl. ..................................... 568/618; 568/608; 568/620; 568/45; 260/410.6; 560/100; 560/209; 560/240; 564/475; 564/399
[58] Field of Search ................. 568/618, 608, 620, 45; 260/410.6; 560/200, 209, 240; 564/475, 399

[56] References Cited

U.S. PATENT DOCUMENTS 4,239,917 12/1980 Yang .................................... 568/618
4,453,023 6/1984 McCain et al. ...................... 568/618

*Primary Examiner*—Howard T. Mars

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of the compound barium phosphate. The product alkoxylates are known to be useful, for instance, as nonionic surfactants, wetting and emulsifying agents, solvents, and chemical intermediates.

66 Claims, No Drawings

ALKOXYLATION PROCESS CATALYZED BY BARIUM PHOSPHATE

This is a continuation of application Ser. No. 07/354,050 filed May 19, 1989, now abandoned.

BACKGROUND OF THE INVENTION

This invention relates to an alkoxylation process in which one or more alkylene oxides are reacted with one or more compounds having active hydrogen atoms in the presence of a catalytically effectively quantity of the compound barium phosphate. In certain preferred embodiments, the invention relates to processes for the preparation of alkoxylate products having utility as nonionic surfactants.

A large variety of products useful, for instance, as nonionic surfactants, wetting and emulsifying agents, solvents, lubricants and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula II) to a single alkanol molecule (formula I) is presented by the equation

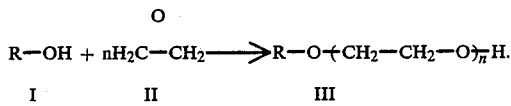

$$\text{R—OH} + n\text{H}_2\text{C—CH}_2 \longrightarrow \text{R—O}\!\!-\!\!(\text{CH}_2\text{—CH}_2\text{—O})_{\overline{n}}\text{H}.$$

I    II    III

A given alkoxylation process typically results in the production of a mixture of alkoxylate molecules having different numbers of alkylene oxide molecules, e.g., molecules having different values for the adduct number "n" in formula III in the above illustration.

The present invention particularly relates to an alkoxylation process wherein the alkylene oxide addition reaction is catalyzed by the compound barium phosphate, $Ba_3(PO_4)_2$.

Various compounds of barium and of the other alkaline earth elements are known as alkoxylation catalysts. For instance, it has been reported (e.g., in U.S. Pat. Nos. 3,752,857, No. 4,134,854, No. 4,223,164, No. 4,306,093 and No. 4,239,917, and in published European Patent Applications 0026544, 0026546, and 0026547) that certain compounds of barium, strontium, and calcium catalyze alkoxylation reactions. U.S. Pat. No. 4,210,764 describes the use of cresylic acids to further promote alkoxylation catalyzed by barium compounds. U.S. Pat. No. 4,302,613 discloses catalyst systems which combine barium and strontium compounds with co-catalysts such as calcium oxide, calcium carbide, calcium hydroxide, magnesium metal, magnesium hydroxide, zinc oxide and aluminum metal.

Strong acids, including phosphoric acid, are also known as alkoxylation catalysts.

Of particular relevance to the present invention, U.S. Pat. No. 4,453,023 describes a process which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorous, carbon dioxide, and oxalic acid.

SUMMARY OF THE INVENTION

It has now been found that the compound barium phosphate $Ba_3(PO_4)_2$, is an effective catalyst for the addition reaction of alkylene oxides with organic compounds having active hydrogen atoms.

Accordingly, the present invention is directed to a process for the preparation of alkoxylates of active hydrogen containing organic compounds which comprises contacting an alkylene oxide reactant comprising one or more vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalyst comprising a catalytically effective amount of barium phosphate.

It has been found that an alkoxylation process catalyzed by barium phosphate has benefit in one or more respects over conventional processes catalyzed by other barium compounds.

In one important respect, the process of this invention provides a product having a distribution of alkylene oxide adducts which is distinguishable from the adduct distribution of products of prior art processes utilizing barium and/or phosphorus containing catalysts. Any alkylene oxide addition reaction produces a mixture of various alkoxylate molecules having different numbers of alkylene oxide adducts (e.g., the alkylene oxide adduct number n in the illustration provided by formula III above). As is well known in the art, the distribution of the different alkylene oxide adducts in the product mixture is a factor which in many respects controls the properties of the alkoxylation product, and efforts are made to tailor the distribution of adduct numbers within a product to the product's intended service.

In certain preferred embodiments, the present invention relates to a process characterized by enhanced selectivity for the preparation of particular alkoxylate mixtures, including valuable alkanol alkoxylate mixtures, in which a relatively large proportion of the alkoxylate molecules have a number of alkylene oxide adducts that is within a relatively narrow range of values. For instance, in one such embodiment, the invention is a process for the preparation of ethoxylates of alkanol reactants which comprises contacting an alkanol reactant with an ethoxylate reactant in the presence of an alkoxylation catalyst comprising a catalytically effective amount of barium phosphate. The alkanol ethoxylate product of such a process has an exceptionally narrow ethylene oxide adduct distribution.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

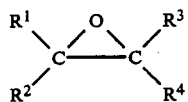

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide, or propylene oxide, or their mixtures. Alkylene oxide reactants consisting essentially of ethylene oxide are considered most preferred from the standpoint of commercial opportunities for the practice of alkoxylation processes, and also from the standpoint of benefits to be gained from the use of the invention to prepare products having unique alkylene oxide adduct distributions.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Preference generally exists for use of hydroxyl-containing reactants. More preferably, the active hydrogen-containing reactant consists essentially of one or more active hydrogen containing compounds selected from the group consisting of alkanols, alkyl polyols and phenols (including alkyl-substituted phenols).

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 3D (preferably from one to about 20) carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent and most preferably greater than about 70 percent of the molecules are of linear (straight-chain) carbon structure.

The general suitability of such alkanols as reactants in alkoxylation reactions is well recognized in the art. Commercially available mixtures of primary mono-hydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, pentaerythritol and the like. Higher oligomers and polymers of the polyols are also very suitable.

The active hydrogen containing reactant is also very suitably the alkoxylate product of a previous alkoxylation of an active hydrogen containing compound. Thus, for example, advantages associated with the invention can be realized by applying the invention to further ethoxylate an alkanol ethoxylate which has previously been prepared by ethoxylation of an alkanol ethoxylate in the presence of a barium phosphate catalyst or another alkoxylation catalyst.

Further examples of both specific alkylene oxide reactants and specific active hydrogen containing reactants suitable for use in this invention are recited in the aforementioned U.S. Patents, the relevant disclosures of which are incorporated herein by this reference.

In general terms, for purposes of the invention, the alkylene oxide reactant and the active hydrogen reactant are necessarily contacted in the presence of a catalytically effective amount of the compound barium phosphate, that is, an amount sufficient to influence the activity and/or the selectivity of the alkoxylation reaction.

It is critical to the invention that the catalyst comprise a catalytically effective amount of the specific compound barium phosphate, For purposes of this specification barium phosphate means the compound of the formula $Ba_3(PO_4)_2$, which has been referred to as tribarium orthophosphate and also as barium tri-orthophosphate. This compound is to be distinguished from barium di-orthophosphate (also known a barium hydrogen phosphate and having the formula $BaHPO_4$) as well as from other phosphate salts of barium. In this regard, the process of this invention is also distinguished from prior art processes which have used other catalysts comprising barium and/or phosphate compounds. In particular, the process of this invention is distinguishable from that disclosed in U.S. Pat. No. 4,453,023, wherein alkoxylation is carried out in the presence of a barium catalyst selected from the group consisting of barium alkoxides, barium phenoxides, barium hydroxides and mixtures thereof, and a promoter which is suitably phosphoric acid. X-ray diffraction analyses of the barium compounds formed upon the combination of a barium compound and phosphoric acid as taught by U.S. Pat. No. 4,453,023 indicate the presence of barium hydrogen phosphate, barium carbonate and barium oxide. This analysis fails to detect a measurable amount of barium phosphate. Although the catalyst described in U.S. Pat. No. 4,453,023 promotes alkoxylation, its alkoxylation performance, in terms of process activity and selectivity, is readily distinguishable from the performance of barium phosphate in the process of this invention.

Barium phosphate for use in this invention is suitably synthesized by neutralization of barium hydroxide or oxide with phosphoric acid in an aqueous medium. For instance, phosphoric acid, preferably in dilute aqueous solution, may simply be added, preferably with mixing, to a solution or slurry of barium hydroxide in water at room temperature. For formation of barium phosphate in this manner, the barium compound and the phosphoric acid are mixed in a molar ratio of 3:2, or, equivalently, 1.5:1, to correspond with the stoichiometry of the formula $(Ba_3(PO_4)_2$. It has been observed that barium and phosphorus containing products other than barium phosphate may be formed during addition of the acid to the barium base, if the local concentration of the acid exceeds that of the base in the aqueous medium. Therefore, gradual addition of the acid to a well-stirred aqueous base is preferred. It is also preferred to add the acid at a rate sufficient to fully neutralize the base to barium phosphate before partially neutralized salts precipitate from solution. It is considered desirable to continue stirring of the mixture after neutralization in order to promote crystallization of the salt product. The product can be recovered by precipitation. Preferred steps for recovery of the salt include isolating by filtration, washing with water, and drying under vacuum. Essentially complete drying is particularly preferred, e.g., under vacuum at elevated temperature. Drying temperature is not critical, although temperatures which allow for pyrophosphate formation (e.g., 600° C.) should be avoided.

The method for preparing barium phosphate as described above is not critical to this invention, and other methods will be apparent to those skilled in the art. It has, however, been observed that the contact between a barium base catalyst and a phosphoric acid catalyst promoter in an alcohol solution, as described in U.S. Pat. No. 4,453,023, is not suitable for barium phosphate preparation. The presence of the alcohol appears to inhibit full neutralization of the acid and the base, and instead favors the production of partially neutralized species such as barium hYdrogen phosphate $BaH(PO_4)$.

Barium phosphate is present in a catalytically-effective amount in the alkoxylation reaction mixture of the process of the invention, that is, in an amount which has a meaningful influence upon alkoxylation reaction activity and/or selectivity. Preferred for practice of the invention is a quantity of barium phosphate which is at least about 0.1 %w (percent by weight), calculated on the weight of the active hydrogen containing reactant. More preferred is the use of the catalyst in a quantity which is between about 0.2 and 5 %w, while a quantity of catalyst in the range from about 0.5 to 2 %w is considered most preferred, particularly for processes involving mono-hydric alkanol and ethylene oxide reactants. Substantially greater quantities of catalyst are also suitable, for instance up to 10 %w, calculated on active hydrogen reactant. As a rule, the higher the desired average alkylene oxide adduct number of the alkoxylate product and the higher the desired rate of reaction, the greater the required quantity of catalyst.

In addition to a catalytically effective amount of the barium phosphate, the catalyst for the process of the invention may also suitably contain other substances, including both those which may be introduced into the process as impurities in the barium phosphate catalyst as well as those which may be added to promote or modify catalyst activity. In one particular respect, it is suitable to apply in the process of this invention a catalyst which comprises other barium compounds in addition to the specified barium phosphate. However, since other compounds of barium which are known as alkoxylation catalysts do not exhibit the activity and/or selectivity of barium phosphate, it is considered preferable that the barium compounds contained in the catalyst be predominantly in the form of barium phosphate. In other words, in such a case, it is preferred that the compound barium phosphate account for a major portion, by weight, of all barium compounds in the catalyst. More preferably, the compound barium phosphate accounts for essentially all of the barium content of the catalyst.

Most preferably, the catalyst applied in the process of this invention consists essentially of barium phosphate.

In general, such specifications and preferences regarding barium phosphate relate to the catalyst in the form in which it is introduced into contact with reactants at the start of an alkoxylation process according to the invention. As is known in this art, the initially introduced catalyst in an alkoxylation process may be converted in whole or in part to other catalytically active or inactive species during the course of the alkoxylation. Thus, the invention is considered to encompass an alkoxylation process carried out in the presence of a catalytically effective amount of barium phosphate, as well as a process carried out in the presence of catalytically effective amounts of one or more other active substances to which barium phosphate may be converted in situ in the alkoxylation reaction mixture. In order to minimize the in situ conversion of barium phosphate to barium hydrogen phosphate and other barium compounds which are not effective for the objects of this invention, it is desirable to maintain a substantially neutral pH for the process reaction mixture.

The catalyst, as well as the reactants, are preferably substantially free of water. The presence of significant amounts of water in the process (e.g., greater than about 500 ppm water based on active hydrogen containing reactant) has been observed to lower catalyst activity and to change the alkylene oxide adduct distribution of the product. Preferably, water content is held below about 200 ppm, calculated on active hydrogen containing reactant. In a preferred mode of practice of the invention, water is removed from a mixture of active hydrogen reactant and catalyst, by heating under vacuum (e.g. a pressure less than about 100 torr) prior to contact with alkylene oxide reactant.

In terms of processing procedures, the alkoxylation reaction in the invention may be conducted in a generally conventional manner. For example, the catalyst may initially be mixed with liquid active hydrogen reactant. The mixture of catalyst and liquid reactant is contacted, preferably under agitation, with alkylene oxide reactant, which is typically introduced in gaseous form, at least for the lower alkylene oxides. The order in which the reactants and catalyst are contacted has not been found to be critical to the invention.

While these procedures describe a batch mode of operation, the invention is equally applicable to a continuous process.

The catalyst may be either soluble (either partially or completely) or insoluble in this liquid reactant as well as in liquid mixtures of the reactant and the product formed as the process is carried out. While it is not intended to limit the scope of the invention to one theory or mechanism of operation, it is believed that the presence of crystalline barium phosphate in the alkoxylation mixture has a beneficial influence upon the performance of the catalyst, particularly on the reaction rate and the alkylene oxide adduct distribution of the product.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater, although the invention is also suitable for alkoxylation of reactants, such as polyols, for which substantially higher average adduct number products are often desired. In particularly preferred embodiments, the invention is applied for the manufacture of ethylene oxide adducts of primary mono-hydric alkanols in the carbon number range from 6 to 24, having an average of between about 1 to 15, more preferably between about 2 and 12, oxyethylene groups per ethoxylate molecule, and characterized by very desirable adduct distribution.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours.

After the ethoxylation reaction has been completed, the product is preferably cooled. If desired, catalyst can be removed from the final product, although catalyst removal is not necessary to the process of the invention. Catalyst residues may be removed, for example, by filtration, centrifugation, extraction, or the like. The fact that a high degree of removal of catalyst residues can be accomplished by physical means suggests that the active catalyst species is essentially insoluble in the reaction mixture.

In certain preferred embodiments, the level of catalyst residues and in some cases the quantity of by-products in the reaction product are reduced by treatment of the alkoxylation reaction product with a material selected from the group consisting of strong acids (particularly oxalic acid and/or phosphoric acid), alkali metal carbonates and bicarbonates, solid organic acids, zeolites (particularly Y zeolite and mordenite), and clays. The products are contacted with one or more of such materials and then filtered, preferably at elevated temperature, e.g., 100° C. An aqueous wash of the product at a temperature of about 125° C. has also been found to be particularly useful for removal of catalyst residues and by-products.

The process of the invention may be applied to the preparation of products having very desirable alkylene oxide adduct distributions, and, in many cases, products for which the adduct distribution differs substantially from that produced by related prior art alkoxylation catalysts. In addition, the process produces a product having a relatively low content of unreacted (residual) active hydrogen reactant, that is a relatively low content of material for which the adduct number is zero. A high level of residual reactant either represents a loss of valuable reactant, or requires that further processing of the product be carried out to recover the reactant. Moreover, the presence of the unreacted material is often of disadvantage from the standpoint of product quality and environmental concerns. For instance, residual alkanol in a detergent alcohol ethoxylate product contributes to volatile organic emissions during spray drying of detergent formulations. Still further, the process of the invention is capable of providing a product having a relatively low content of polyalkylene glycols and other by-products. Moreover, the polyalkylene glycol by-products which do result from practice of this invention are generally of a relatively high carbon number than the by-products of conventional alkoxylation processes, and are more readily separated from the principal alkoxylation products by physical means such as filtration, centrifugation, and the like.

The following Examples are provided to further illustrate certain specific aspects of the invention but are not intended to limit its broader scope.

Example 1

Barium phosphate was prepared by the following procedure. Barium hydroxide monohydrate (15.0 g, 79.2 mmoles) was dissolved in 1500 ml of distilled water under stirring for one hour. Phosphoric acid (6.1 grams of 85%w phosphoric acid, containing 52.8 mmoles of the acid) was diluted with 100 ml of distilled water and the dilute acid solution was then added dropwise to the barium hydroxide solution over an eight minute period. A milky white suspension formed and remained. The suspension was stirred for two hours and then filtered through a Buchner funnel, washed with 600 ml of distilled water, and filtered to dryness. The precipitate was placed in a vacuum oven at 120° C. at a pressure of 20 mm mercury for several hours to effect more complete dryness. The white solid was analyzed by X-ray powder diffraction and found to contain $Ba_3(PO_4)_2$ as the only crystalline product.

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a registered trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 2.50 grams of the barium phosphate prepared as described above was added to 110 grams of NEODOL 23 Alcohol, and the mixture was transferred to a 500 ml autoclave reactor maintained under nitrogen atmosphere. The autoclave and its contents were then heated to 155° C. under a constant nitrogen sparge to drive off water. The mixture was held at 155° C. for 10-15 minutes. A mixture of nitrogen and ethylene oxide was then introduced into the reactor to a total pressure of 60 psia (30 psia nitrogen and 30 psia ethylene oxide). Alkoxylation (ethoxylation) commenced immediately. Additional ethylene oxide was supplied on demand to maintain an essentially constant 30 psia ethylene oxide partial pressure. Temperature was maintained at 155° C. A total of 180 grams of ethylene oxide was taken up over a period of 2.75 hours. The reactor was maintained at temperature for an additional one-half hour to consume unreacted ethylene oxide.

The product was analyzed by GC-LC techniques and found to have a mean average adduct number of 6.9. The ethylene oxide adduct distribution of the product is presented in the following table. The only observed byproducts were polyethylene glycols (PEG) in a quantity of 2.3% weight.

| ETHOXYLATE DISTRIBUTION | |
| --- | --- |
| Adduct Number | Concentration |
| 0 | 1.8% w |
| 1 | 0.4% w |
| 2 | 0.6% w |
| 3 | 1.3% w |
| 4 | 2.8% w |
| 5 | 6.3% w |
| 6 | 12.3% w |
| 7 | 18.7% w |
| 8 | 21.2% w |
| 9 | 17.1% w |
| 10 | 10.2% w |
| 11 | 4.7% w |
| 12 | 1.7% w |

-continued

| ETHOXYLATE DISTRIBUTION | |
|---|---|
| Adduct Number | Concentration |
| 13 | 0.6% w |
| 14 | 0.2% w |
| 15 | 0.1% w |

Example 2

Barium phosphate was prepared by the following procedure. Barium hydroxide monohydrate (20.0 g, 105.6 mmoles) was dissolved in 3000 ml of distilled water with stirring for a few minutes. Phosphoric acid (8.1 g of 85%w phosphoric acid, containing 70.4 mmoles of the acid) was diluted with 100 ml of distilled water and the dilute acid was added dropwise to the barium hydroxide solution over a ten minute period. A milky white suspension formed and remained as the mixture was stirred for four hours. A solid was recovered upon filtration through a Buchner funnel, washed with 1200 ml of distilled water, and filtered to dryness. The solid was placed in a vacuum oven at 120° C. and 20mm of mercury for several hours to effect more complete dryness. The white solid was analyzed by X-ray powder diffraction and found to contain $Ba_3(PO_4)_2$ as the only crystalline product.

An alkoxylation process in accordance with the invention was conducted under the same general procedures described for example 1, using as alkoxylation catalyst the barium phosphate prepared as described above. At a reaction temperature of 155° C., a total of 180 grams of ethylene oxide was taken up over a period of 6.0 hours. The product was analyzed by GC-LC techniques and found to have a mean average adduct number of 7.5. The ethylene oxide adduct distribution of the product is presented in the following table. The only observed by-products were polyethylene glycols.

| ETHOXYLATE DISTRIBUTION | |
|---|---|
| Adduct Number | Concentration |
| 0 | 1.1% w |
| 1 | 0.3% w |
| 2 | 0.3% w |
| 3 | 0.7% w |
| 4 | 1.6% w |
| 5 | 4.5% w |
| 6 | 10.5% w |
| 7 | 18.9% w |
| 8 | 23.1% w |
| 9 | 19.2% w |
| 10 | 11.4% w |
| 11 | 5.0% w |
| 12 | 1.8% w |
| 13 | 0.7% w |
| 14 | 0.4% w |
| 15 | 0.2% w |
| 16 | 0.2% w |

Example 3

Barium phosphate was prepared by the following procedure. Barium hydroxide monohydrate (5.0 g, 26.4 mmoles) was dissolved in 3000 ml of distilled water and allowed to stir for one hour. Phosphoric acid (2.0 g of 85%w phosphoric, containing 17.6 mmoles of the acid) was diluted with 100 ml of distilled water and added dropwise to the barium hydroxide solution over an eight minute period. A milky white suspension formed and remained as the suspension was stirred for four hours. The suspension was filtered through a Buchner funnel to recover solid which was washed with 1200 ml of distilled water and filtered to dryness. The solid was placed in a vacuum oven at 120° C. and 20mm of mercury for several hours to effect more complete dryness. The white solid was analyzed by X-ray powder diffraction and found to contain $Ba_3(PO_4)_2$ as the only crystalline product.

An alkoxylation process in accordance with the invention was conducted under the same general procedures described for examples 1 and 2, using as alkoxylation catalyst the barium phosphate prepared as described above. At a reaction temperature of 155° C., a total of 180 grams of ethylene oxide was taken up over a period of 1.0 hour. The product was analyzed by GC-LC techniques and found to have a mean average adduct number of 6.7. The ethylene oxide adduct distribution of the product is presented in the following table. The only observed by-products were polyethylene glycols.

| ETHOXYLATE DISTRIBUTION | |
|---|---|
| Adduct Number | Concentration |
| 0 | 2.0% w |
| 1 | 0.6% w |
| 2 | 0.8% w |
| 3 | 1.7% w |
| 4 | 3.8% w |
| 5 | 8.3% w |
| 6 | 14.6% w |
| 7 | 20.1% w |
| 8 | 20.1% w |
| 9 | 14.8% w |
| 10 | 8.1% w |
| 11 | 3.3% w |
| 12 | 1.2% w |
| 13 | 0.4% w |
| 14 | 0.2% w |
| 15 | 0.1% w |
| 16 | 0.0% w |

Example 4 (18968-161A)

Barium phosphate was prepared by the following procedure. Barium hydroxide monohydrate (45.0 g, 237.6 mmoles) was dissolved in 3000 ml of distilled water with stirring for two hours. Phosphoric acid (18.3 g of 85%w phosphoric acid containing 158.5 mmoles of the acid) was added dropwise to the barium hydroxide solution over a seven minute period. A milky white suspension formed. The suspension was then immediately filtered through a Buchner funnel to recover a solid which was washed with 400 ml of distilled water and filtered to dryness. The solid was then heated to 120° C. under a 20mm of mercury vacuum for several hours to effect more complete dryness. The white solid was analyzed by X-ray powder diffraction and found to contain $Ba_3(PO_4)_2$ as the major crystalline product, with much smaller amounts of crystalline $BaHPO_4$ and $Ba_5(OH)(PO_4)_3$ also present.

An alkoxylation process in accordance with the invention was conducted under the same general procedures described for examples 1, using as alkoxylation catalyst the barium phosphate prepared as described above. At a reaction temperature of 155° C., a total of 180 grams of ethylene oxide was taken up over a period of 2.8 hours. The product was analyzed by GC-LC techniques and found to have a mean average adduct number of 7.1. The ethylene oxide adduct distribution of the product is presented in the following table. The only observed by-products were polyethylene glycols.

| ETHOXYLATE DISTRIBUTION | |
|---|---|
| Adduct Number | Concentration |
| 0 | 2.0% w |
| 1 | 0.5% w |
| 2 | 0.6% w |
| 3 | 1.3% w |
| 4 | 2.9% w |
| 5 | 6.4% w |
| 6 | 11.5% w |
| 7 | 17.4% w |
| 8 | 19.8% w |
| 9 | 16.6% w |
| 10 | 10.7% w |
| 11 | 5.5% w |
| 12 | 2.6% w |
| 13 | 1.2% w |
| 14 | 0.6% w |
| 15 | 0.3% w |
| 16 | 0.2% w |

Example 5

Barium phosphate was prepared by the following procedure. Barium hydroxide monohydrate (45.0 g, 237.6 mmoles) was dissolved in 3000 ml of distilled water and stirred for two hours. Phosphoric acid (18.3 g of 85%w phosphoric acid, containing 158.5 mmoles of acid) was added dropwise to the barium hydroxide solution over a seven minute period. A milky white suspension formed and remained as the suspension was stirred for one hour. The mixture was then filtered through a Buchner funnel to recover a solid which was washed with 400 ml of distilled water and filtered to dryness. The solid was placed in a vacuum oven at 120° C. and 20mm of mercury for several hours to effect more complete dryness. The white solid product was analyzed by X-ray powder diffraction and found to contain $Ba_3(PO_4)_2$ as the major crystalline product, with much smaller amounts of crystalline $BaHPO_4$ and $Ba_5(OH)(PO_4)_3$ also present.

An alkoxylation process in accordance with the invention was conducted under the same general procedures described for examples 1, using as alkoxylation catalyst the barium phosphate prepared as described above. At a reaction temperature of 155° C., a total of 180 grams of ethylene oxide was taken up over a period of 2.0 hours. The product was analyzed by GC-LC techniques and found to have a mean average adduct number of 7.4. The ethylene oxide adduct distribution of the product is presented in the following table. The only observed by-products were polyethylene glycols.

| ETHOXYLATE DISTRIBUTION | |
|---|---|
| Adduct Number | Concentration |
| 0 | 1.8% w |
| 1 | 0.4% w |
| 2 | 0.4% w |
| 3 | 0.8% w |
| 4 | 1.7% w |
| 5 | 4.0% w |
| 6 | 8.9% w |
| 7 | 17.8% w |
| 8 | 25.4% w |
| 9 | 19.7% w |
| 10 | 11.3% w |
| 11 | 5.0% w |
| 12 | 1.8% w |
| 13 | 0.6% w |
| 14 | 0.3% w |
| 15 | 0.2% w |
| 16 | 0.0% w |

Example 6 (18826-154-1)

Barium phosphate was prepared by the following procedure. Barium hydroxide monohydrate (1080 g, 5.70 moles) was dissolved in 27 gallons of distilled water and allowed to stir for 15 minutes. Phosphoric acid (439 g of 85%w phosphoric acid, containing 3.81 moles of the acid) was added dropwise to the barium hydroxide solution over a seven minute period. A milky white suspension formed. The suspension was stirred for three hours and then filtered through a Buchner funnel to recover a solid which was washed with 10 gallons of distilled water, and filtered to dryness. The solid was placed in a vacuum oven at 120° C. and 20mm of mercury for several hours to effect more complete dryness. The white solid product was analyzed by X-ray powder diffraction and found to contain $Ba_3(PO_4)_2$ as the only crystalline product.

An alkoxylation process in accordance with the invention was conducted under the same general procedures described for examples 1, using as alkoxylation catalyst the barium phosphate prepared as described above. At a reaction temperature of 155° C., a total of 180 grams of ethylene oxide was taken up over a period of 3.25 hours. The product was analyzed by GC-LC techniques and found to have a mean average adduct number of 7.8. The ethylene oxide adduct distribution of the product is presented in the following table. The only observed by-products were polyethylene glycols.

| ETHOXYLATE DISTRIBUTION | |
|---|---|
| Adduct Number | Concentration |
| 0 | 1.8% w |
| 1 | 0.3% w |
| 2 | 0.4% w |
| 3 | 0.8% w |
| 4 | 1.5% w |
| 5 | 3.5% w |
| 6 | 7.3% w |
| 7 | 13.9% w |
| 8 | 19.9% w |
| 9 | 20.4% w |
| 10 | 15.5% w |
| 11 | 8.7% w |
| 12 | 3.9% w |
| 13 | 1.4% w |
| 14 | 0.5% w |
| 15 | 0.3% w |
| 16 | 0.0% w |

Example 7

Barium phosphate was prepared by the following procedure. Barium hydroxide monohydrate (30.0 g, 158.4 mmoles) was dissolved in 3000 ml of distilled water and stirred for one hour. Phosphoric acid (12.2 g of 85%w phosphoric acid, containing 105.6 mmoles of acid) was diluted with 200 ml of distilled water and the resulting solution was added dropwise to the barium hydroxide solution over a seven minute period. A milky white suspension formed. The suspension was stirred for five hours and then filtered through a Buchner funnel to recover a solid which was washed with 1200 ml of distilled water, and filtered to dryness. The solid was further dried in a vacuum oven at 120° C. and 20mm of mercury for several hours. The white solid product was analyzed by X-ray powder diffraction and found to contain $Ba_3(PO_4)_2$ as the only crystalline product.

An alkoxylation process in accordance with the invention was conducted under the same general procedures described for examples 1, but at a lower temperature. For this example, 3.46 grams of the barium phosphate prepared as described above was added to 154 grams of the alcohol, and the mixture was transferred to a 1000 ml autoclave reactor under nitrogen atmosphere. The autoclave and its contents were then heated up to 155° C. under a constant nitrogen sparge to drive off water. The autoclave was cooled to 130° C. for the alkoxylation reaction. A total of 256 grams of ethylene oxide was taken up over a period of 2.16 hours. The product was analyzed by GC-LC techniques and found to have a mean average adduct number of 7. The ethylene oxide adduct distribution of the product had a maximum of 19.2%w. The only observed by-products were polyethylene glycols in a quantity of 0.8%w.

Example 8

Barium phosphate was prepared by the following procedure. Barium hydroxide monohydrate (30.0 g, 158.4 mmoles) was dissolved in 3000 ml of distilled water and stirred for one hour. Phosphoric acid (12.2 g of 85%w phosphoric acid, containing 105.6 mmoles of the acid) was diluted with 200 ml of distilled water and the resulting solution was added dropwise to the barium hydroxide solution over a seven minute period. A milky white suspension formed. The suspension was stirred for four hours and then filtered through a Buchner funnel to recover a solid which was washed with 1200 ml of distilled water, and filtered to dryness. The solid was further dried in a vacuum oven at 120° C. and 20mm of mercury for several hours. The white solid was analyzed by X-ray powder diffraction and found to contain $Ba_3(PO_4)_2$ as the only crystalline product.

An alkoxylation process in accordance with the invention was conducted under the same general procedures described for example 1, but applying a lesser amount of catalyst. For this example, 1.80 grams of the barium phosphate prepared as described above was added to 156 grams of the alcohol, and the mixture was transferred to a 1000 ml autoclave reactor under nitrogen atmosphere. The autoclave and its contents were then heated up to 155° C. under a constant nitrogen sparge to drive off water. A mixture of nitrogen (30 psia) and ethylene oxide (30 psia) was introduced. Alkoxylation commenced immediately., additional ethylene oxide was supplied on demand to maintain the 60 psia total pressure. Temperature was maintained at 155° C. A total of 195 grams of ethylene oxide was taken up over a period of 3.62 hours. The product was analyzed by GC-LC techniques and found to have a mean average adduct number of 5.4. The ethylene oxide adduct distribution of the product peaked at 20.9%w. The only observed by-products were polyethylene glycols in a quantity of 1.5%w.

Comparative Experiments A-E

A series of experiments were carried out, to compare the process of this invention with that of U.S. Pat. No. 4,453,023.

The general procedures of the examples of U.S. Pat. No. 4,453,020 (particularly those of example 6 of the patent) were followed to prepare phosphoric acid-promoted, barium alkoxylation catalysts, and to use these promoted catalysts for ethoxylation of a higher carbon number primary alkanol.

For each of the series of comparative experiments, 3.02 grams of barium hydroxide (monohydrate) was added to 110 grams of the NEODOL 23 Alcohol. This mixture was heated to 110° C. and maintained at that temperature and under vacuum (0.5 torr) for one hour. After cooling, phosphoric acid (0.506 grams) was then added, with stirring, to the mixture for comparative experiment A. The amount of phosphoric acid added was varied in the other comparative experiments as described below. The resulting mixture was heated at 110° C. under vacuum for one hour, cooled, placed in an autoclave under nitrogen atmosphere and contacted and reacted with ethylene oxide at a temperature of 140° C.

For comparative experiment A, the barium hydroxide catalyst and the phosphoric acid promoter were applied in a relative molar ratio of 3.6:1. Greater quantities of phosphoric acid were added in experiments B, C, D, and E. The quantity of phosphoric acid added in experiments C and D corresponds to the molar ratio of 1.5 and thus to the stoichiometry of the formation of the barium phosphate $Ba_3(PO_4)_2$ catalyst applied in the process of this invention.

For the process which it describes and claims, U.S. Pat. No. 4,453,023 teaches the use of a catalyst promoter, e.g., phosphoric acid, in a concentration which is up to about 30% by weight, calculated on the weight of barium salt employed. The molar ratios of 3.6 and 2.5 for experiments A and B correspond to phosphoric acid concentrations (calculated on this same basis) of 15.8% by weight and 22.8% by weight respectively, and are within the teachings of the patent. The molar ratio of 1.5 applicable to the comparative experiments C and D (as well as to the preparation of the different catalyst of the present invention) correspond to a phosphoric acid concentration of 38% by weight, outside of the teachings of U.S. Pat. No. 4,453,023.

The results of these comparative experiments, presented in the following table, are readily distinguishable from those of the process of this invention. Most notably, when the barium hydroxide and phosphoric acid components are introduced into the reactor in a molar ratio of 1.5, in experiments C and D, the neutralization product is inactive as an alkoxylation catalyst. At greater molar ratios, in experiments A and B, the process does produce an alkoxylation product, although one characterized by a different adduct distribution (in this case, a broader and less peaked adduct distribution) than that produced by practice of the process of this invention.

| Comparative Experiment | Molar Ratio of Barium Alkoxide to Phosphoric Acid | EO Added (grams) | Reaction Time (min.) | Product Avg. Adduct Number | Distribution Peak Maximum |
|---|---|---|---|---|---|
| A | 3.6 | 180 | 90 | 6.8 | 14.4 |
| B | 2.5 | 180 | 125 | 6.7 | 15.2 |
| C | 1.5(a) | 9(b) | 95 | 0 | — |
| D | 1.5(a) | 13(b) | 90 | 0 | — |

-continued

| Comparative Experiment | Molar Ratio of Barium Alkoxide to Phosphoric Acid | EO Added (grams) | Reaction Time (min.) | Avg. Adduct Number | Product Distribution Peak Maximum |
|---|---|---|---|---|---|
| E | 1.0 | 10$^{(b)}$ | 90 | 0 | — |

$^{(a)}$a molar ratio of 1.5 corresponds to the stoichiometric ratio for formation of barium phosphate
$^{(b)}$initial fill of the reactor requires approximately 10 grams of ethylene oxide Analysis by X-ray diffraction of the barium species formed under the practice of the procedures described in the examples of U.S. Pat. No. 4,453,023 indicated the presence of barium hydrogen phosphate $BaHPO_4$, barium carbonate $BaCO_3$, and barium/oxygen species including barium oxide. These analyses failed to detect barium phosphate $Ba_3(PO_4)_2$. In comparative experiments C and D, the analysis indicated that for the inactive catalyst the barium compounds consisted essentially of barium hydrogen phosphate.

Example 9

Barium phosphate was prepared by the following procedure. Barium hydroxide (31.23 grams of Ba(OH)$_2$8H$_2$O, 0.099 moles) was dissolved in 500 grams of deionized water and added to a 1 liter reaction flask fitted with a magnetic stirring bar, reflux condensor and dropping funnel. The hazy solution was heated to 68° C., and treated dropwise over a 30 minute period with a solution of 7.61 grams of 85%w phosphoric acid (0.066 moles of acid) in 50 grams of deionized water. The resulting milky white mixture was heated further at 80° C. for an additional two hours, then cooled to 25° C. and filtered using a medium porosity glass filter. The white filter cake was washed several times with deionized water until the wash was approximately neutral pH. The solid was dried under vacuum (80mm Hg) at 80° C. for 24 hours. Analysis of the product showed 63 %w Ba and 8.9 %w P (theoretical for $Ba_3(PO_4)_2$ is 68.4% Ba and 10.3 %w P), with the remainder presumably water.

An alkoxylation process in accordance with the invention was carried out for the ethoxylation of the NEODOL 23 Alcohol. A total of 200.2 grams (1.032 moles) of the alcohol, predried to a water content of 120 ppm, was added to a one liter autoclave. Then 3.0 grams of the barium phosphate prepared as described above was added, the reactor was sealed and placed under a nitrogen atmosphere and heated with stirring to 155° C. A mixture of 40 %m (percent by mole) of ethylene oxide and 60 %m nitrogen was added as the reaction proceeded. A total of 371 grams (7.4 moles) of ethylene oxide was added as pressure in the reactor increased to 125 psia. The reaction mixture was stirred at 155° C. for an additional hour to consume unreacted ethylene oxide, and then cooled to 25° C.

The average ethylene oxide adduct number of the product of this process was determined by GC-LC methods to be 7.05. The adduct distribution of the product in presented in the following table.

| ETHOXYLATE DISTRIBUTION | |
|---|---|
| Adduct Number | Concentration |
| 0 | 2.1% w |
| 1 | 0.6% w |
| 2 | 0.9% w |
| 3 | 1.7% w |
| 4 | 3.1% w |
| 5 | 6.2% w |
| 6 | 10.9% w |
| 7 | 16.2% w |
| 8 | 19.0% w |
| 9 | 17.1% w |
| 10 | 12.0% w |
| 11 | 6.4% w |
| 12 | 2.7% w |
| 13 | 0.9% w |
| 14 | 0.2% w |
| 15 | 0.1% w |

Example 10

Barium phosphate was prepared as described in example 10 was used to catalyze the alkoxylation of a secondary alkanol reactant. A total of 192.4 grams (1.07 moles) of a mixture of predominantly linear secondary alkanols having eleven and twelve carbon atoms (about 45% by mole $C_{11}$ and about 55% by mole $C_{12}$) was dried to less than 150 ppm water and added to a one liter autoclave under nitrogen atmosphere. After addition of 2.0 grams of the barium phosphate catalyst to the reactor, it was sealed and heated to 170° C. A mixture of 40 %m (percent by mole) of ethylene oxide and 60 %m nitrogen was added to the stirred reactor as the reaction proceeded. A total of 329 grams of ethylene oxide was added over a 194 minute period. The reaction mixture was stirred at 170° C. for an additional 41 minutes to consume unreacted ethylene oxide, and then cooled to 25° C.

The average ethylene oxide adduct number of the product of this process was determined by GC-LC methods to be 6.7. The adduct distribution of the product in presented in the following table.

| ETHOXYLATE DISTRIBUTION | |
|---|---|
| Adduct Number | Concentration |
| 0 | 16.8% w |
| 1 | 1.4% w |
| 2 | 0.4% w |
| 3 | 0.6% w |
| 4 | 0.7% w |
| 5 | 0.9% w |
| 6 | 1.2% w |
| 7 | 1.6% w |
| 8 | 2.1% w |
| 9 | 2.9% w |
| 10 | 3.9% w |
| 11 | 5.1% w |
| 12 | 6.9% w |
| 13 | 8.8% w |
| 14 | 10.3% w |
| 15 | 10.7% w |
| 16 | 9.9% w |
| 17 | 7.4% w |
| 18 | 4.7% w |
| 19 | 2.5% w |
| 20 | 1.0% w |
| 21 | 0.4% w |

Example 11

Another ethoxylation process was carried out with a secondary alkanol reactant. In this case, the barium phosphate catalyst was that prepared as described in example 2 above. For this process, a slurry of 2.0 grams of the barium phosphate in 200 grams of the mixed $C_{11}/C_{12}$ secondary linear alkanols (predried to less than 200 ppm water) was added to a one liter autoclave reactor under nitrogen atmosphere. The reactor was sealed and heated to 170° C. A mixture of 40 %m (percent by mole) of ethylene oxide in nitrogen was added to the stirred reactor as the reaction proceeded. A total of 342 grams of ethylene oxide was added over a 244 minute period. The reaction mixture was stirred at 170° C. for an additional hour to consume unreacted ethylene oxide, and then cooled to 25° C.

The average ethylene oxide adduct number of the product of this process was determined by GC-LC methods to be 7.1. The adduct distribution of the product in presented in the following table.

| ETHOXYLATE DISTRIBUTION | |
|---|---|
| Adduct Number | Concentration |
| 0 | 13.8% w |
| 1 | 0.7% w |
| 2 | 0.4% w |
| 3 | 0.7% w |
| 4 | 0.8% w |
| 5 | 1.2% w |
| 6 | 1.6% w |
| 7 | 2.2% w |
| 8 | 3.1% w |
| 9 | 4.4% w |
| 10 | 6.1% w |
| 11 | 8.1% w |
| 12 | 10.1% w |
| 13 | 11.6% w |
| 14 | 11.7% w |
| 15 | 9.8% w |
| 16 | 6.8% w |
| 17 | 3.9% w |
| 18 | 1.8% w |
| 19 | 0.8% w |
| 20 | 0.3% w |

Comparative Experiment F

A process was carried out under the same procedures and conditions of example 11, except for the use of a potassium hydroxide catalyst in place of the barium phosphate catalyst. This process catalyzed by potassium hydroxide does not come within this invention and is provided only to illustrate distinctions between the invention and the prior art with respect to adduct distribution of the product. Secondary alkanol (15 grams) and ethylene oxide (26 grams) were reacted for 360 minutes at a temperature of 150° C. in the presence of 0.056 grams of 85% potassium hydroxide at 1 atmosphere EO partial pressure. The product was characterized by an average ethylene oxide adduct number of 6.4 and had a broad range adduct distribution as shown in the following table.

| ETHOXYLATE DISTRIBUTION | |
|---|---|
| Adduct Number | Concentration |
| 0 | 16.1% w |
| 1 | 1.7% w |
| 2 | 1.6% w |
| 3 | 1.7% w |
| 4 | 1.7% w |
| 5 | 1.8% w |
| 6 | 3.5% w |
| 7 | 3.6% w |
| 8 | 3.6% w |
| 9 | 3.9% w |
| 10 | 4.1% w |
| 11 | 4.3% w |
| 12 | 4.4% w |
| 13 | 4.5% w |
| 14 | 4.5% w |
| 15 | 4.5% w |
| 16 | 4.4% w |
| 17 | 4.3% w |
| 18 | 4.2% w |
| 19 | 4.2% w |
| 20 | 4.0% w |
| 21 | 3.7% w |
| 22 | 3.4% w |
| 23 | 3.3% w |
| 24 | 2.9% w |

Comparative Experiment G

To illustrate the importance of a relatively dry reaction system for purposes of the process of this invention, a process was carried out under conditions and procedures similar to those described in example 10 using a secondary alkanol reactant which had not been predried. The alkanol reactant contained 7565 ppm water. No reaction was observed after 70 minutes contact between the ethylene oxide and the secondary alkanol at a temperature of 170° C.

What is claimed is:

1. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalyst comprising a catalytically effective amount of barium phosphate.

2. The process of claim 1, wherein the alkylene oxide reactant consists essentially of one or more alkylene oxides selected from the group consisting of ethylene oxide and propylene oxide.

3. The process of claim 2, wherein the active hydrogen containing reactant consists essentially of one or more compounds selected from the group consisting of alcohols, phenols and polyols.

4. The process of claim 3, wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

5. The process of claim 4, wherein the active hydrogen containing reactant consists essentially of one or more $C_1$-$C_{30}$ primary mono-hydric alkanols.

6. The process of claim 5, wherein the active hydrogen containing reactant consists essentially of primary mono-hydric alkanols having carbon numbers in the range from 6 to 24, inclusive, and the alkylene oxide reactant consists essentially of ethylene oxide.

7. The process of claim 6, wherein the active hydrogen containing reactant consists essentially of primary mono-hydric alkanols having carbon numbers in the range from 8 to 20, inclusive.

8. The process of claim 7, wherein greater than about 50% of the molecules of the primary mono-hydric alkanols are of linear carbon structure.

9. The process of claim 8, wherein greater than about 70% of the molecules are of linear carbon structure.

10. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a barium containing catalyst wherein a major portion by weight of the barium compounds present are in the form of barium phosphate.

11. The process of claim 10, wherein the alkylene oxide reactant consists essentially of one or more alkylene oxides selected from the group consisting of ethylene oxide and propylene oxide.

12. The process of claim 11, wherein the active hydrogen containing reactant consists essentially of one or more compounds selected from the group consisting of alcohols, phenols and polyols.

13. The process of claim 12, wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

14. The process of claim 13, wherein the active hydrogen containing reactant consists essentially of one or more $C_1$-$C_{30}$ primary mono-hydric alkanols, and the alkylene oxide reactant consists essentially of ethylene oxide.

15. The process of claim 14, wherein the active hydrogen containing reactant consists essentially of primary mono-hydric alkanols having carbon numbers in the range from 6 to 24, inclusive.

16. The process of claim 15, wherein the active hydrogen containing reactant consists essentially of primary mono-hydric alkanols having carbon numbers in the range from 8 to 20, inclusive.

17. The process of claim 16, wherein greater than about 50% of the molecules of the primary mono-hydric alkanols are of linear carbon structure.

18. The process of claim 17, wherein greater than about 70% of the molecules are of linear carbon structure.

19. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of barium phosphate.

20. The process of claim 19, wherein the alkylene oxide reactant consists essentially of one or more alkylene oxides selected from the group consisting of ethylene oxide and propylene oxide, and wherein the active hydrogen containing reactant consists essentially of one or more compounds selected from the group consisting of alcohols, phenols and polyols.

21. The process of claim 20, wherein the active hydrogen containing reactant consists essentially of primary mono-hydric alkanols having carbon numbers in the range from 6 to 24, inclusive, and the alkylene oxide reactant consists essentially of ethylene oxide.

22. The process of claim 21, wherein the active hydrogen containing reactant consists essentially of primary mono-hydric alkanols having carbon numbers in the range from 8 to 20, inclusive, wherein greater than about 70% of the primary mono-hydric alkanol molecules are of linear carbon structure.

23. The process of claim 20, wherein the active hydrogen-containing reactant consists essentially of polyols having from 2 to about 6 hydroxyl groups and the alkylene oxide reactant consists essentially of propylene oxide.

24. The process of claim 19, wherein the barium phosphate is present in an amount which is at least about 0.1 percent by weight, relative to the weight of the active hydrogen reactant.

25. The process of claim 24, wherein the alkylene oxide reactant consists essentially of one or more alkylene oxides selected from the group consisting of ethylene oxide and propylene oxide, and wherein the active hydrogen containing reactant consists essentially of one or more compounds selected from the group consisting of alcohols, phenols and polyols.

26. The process of claim 25, wherein the active hydrogen containing reactant consists essentially of primary mono-hydric alkanols having carbon numbers in the range from 6 to 24, inclusive, and the alkylene oxide reactant consists essentially of ethylene oxide.

27. The process of claim 26, wherein the active hydrogen containing reactant consists essentially of primary mono-hydric alkanols having carbon numbers in the range from 8 to 20, inclusive, wherein greater than about 70% of the primary mono-hydric alkanol molecules are of linear carbon structure.

28. The process of claim 24, wherein the active hydrogen-containing reactant consists essentially of polyols having from 2 to about 6 hydroxyl groups and the alkylene oxide reactant consists essentially of propylene oxide.

29. The process of claim 24, wherein the barium phosphate is present in an amount in the range of from about 0.2 to 5 percent by weight, relative to the weight of the active hydrogen reactant.

30. The process of claim 29, wherein the alkylene oxide reactant consists essentially of one or more alkylene oxides selected from the group consisting of ethylene oxide and propylene oxide, and wherein the active hydrogen containing reactant consists essentially of one or more compounds selected from the group consisting of alcohols, phenols and polyols.

31. The process of claim 30, wherein the active hydrogen containing reactant consists essentially of primary mono-hydric alkanols having carbon numbers in the range from 6 to 24, inclusive, and the alkylene oxide reactant consists essentially of ethylene oxide.

32. The process of claim 31, wherein the active hydrogen containing reactant consists essentially of primary mono-hydric alkanols having carbon numbers in the range from 8 to 20, inclusive, wherein greater than about 70% of the primary mono-hydric alkanol molecules are of linear carbon structure.

33. The process of claim 29, wherein the active hydrogen-containing reactant consists essentially of polyols having from 2 to about 6 hydroxyl groups and the alkylene oxide reactant consists essentially of propylene oxide.

34. The process of claim 1, wherein the alkylene oxide reactant consists essentially of ethylene oxide.

35. The process of claim 34, wherein the active hydrogen-containing reactant consists essentially of one or more primary mono-hydric alkanols having carbon numbers in the range from 8 to 20, inclusive.

36. The process of claim 1, wherein the active hydrogen-containing reactant consists essentially of polyols having from 2 to about 6 hydroxyl groups and the alkylene oxide reactant consists essentially of one or more alkylene oxides selected from the group consisting of propylene oxide and ethylene oxide.

37. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalyst consisting essentially of a catalytically effective amount of barium phosphate.

38. The process of claim 19, wherein the alkylene oxide reactant consists essentially of one or more alkylene oxides selected from the group consisting of ethylene oxide and propylene oxide.

39. The process of claim 38, wherein the active hydrogen containing reactant consists essentially of one or more compounds selected from the group consisting of alcohols, phenols and polyols.

40. The process of claim 39, wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

41. The process of claim 40, wherein the active hydrogen containing reactant consists essentially of one or more $C_1$-$C_{30}$ primary mono-hydric alkanols.

42. The process of claim 41, wherein the active hydrogen containing reactant consists essentially of primary mono-hydric alkanols having carbon numbers in the range from 6 to 24, inclusive, and the alkylene oxide reactant consists essentially of ethylene oxide.

43. The process of claim 42, wherein the active hydrogen containing reactant consists essentially of primary mono-hydric alkanols having carbon numbers in the range from 8 to 20, inclusive.

44. The process of claim 43, wherein greater than about 50% of the molecules of the primary mono-hydric alkanols are of linear carbon structure.

45. The process of claim 44, wherein greater than about 70% of the molecules are of linear carbon structure.

46. The process of claim 39, wherein the active hydrogen-containing reactant consists essentially of polyols having from 2 to about 6 hydroxyl groups and the alkylene oxide reactant consists essentially of propylene oxide.

47. The process of claim 37, wherein the barium phosphate is present in an amount in the range of from about 0.2 to 5 percent by weight, relative to the weight of the active hydrogen reactant.

48. The process of claim 38, wherein the barium phosphate is present in an amount in the range of from about 0.2 to 5 percent by weight, relative to the weight of the active hydrogen reactant.

49. The process of claim 39, wherein the barium phosphate is present in an amount in the range of from about 0.2 to 5 percent by weight, relative to the weight of the active hydrogen reactant.

50. The process of claim 40, wherein the barium phosphate is present in an amount in the range of from about 0.2 to 5 percent by weight, relative to the weight of the active hydrogen reactant.

51. The process of claim 41, wherein the barium phosphate is present in an amount in the range of from about 0.2 to 5 percent by weight, relative to the weight of the active hydrogen reactant.

52. The process of claim 42, wherein the barium phosphate is present in an amount in the range of from about 0.2 to 5 percent by weight, relative to the weight of the active hydrogen reactant.

53. The process of claim 43, wherein the barium phosphate is present in an amount in the range of from about 0.5 to 2 percent by weight, relative to the weight of the active hydrogen reactant.

54. The process of claim 44, wherein the barium phosphate is present in an amount in the range of from about 0.5 to 2 percent by weight, relative to the weight of the active hydrogen reactant.

55. The process of claim 45, wherein the barium phosphate is present in an amount in the range of from about 0.5 to 2 percent by weight, relative to the weight of the active hydrogen reactant.

56. The process of claim 46, wherein the barium phosphate is present in an amount in the range of from about 0.5 to 2 percent by weight, relative to the weight of the active hydrogen reactant.

57. A process for the preparation of ethylene oxide adduct of primary mono-hydric alkanols having carbon numbers in the range from 6 to 24, inclusive, which comprises contacting and reacting gaseous ethylene oxide with one or a mixture of said alkanols in an agitated liquid phase containing no more than about 200 ppm water at a temperature in the range from about 130° C. to 190° C. in the presence of between about 0.2 and 5 percent by weight of barium phosphate, calculated on the weight of the said alkanols.

58. The process of claim 57, wherein the alkanols are in the carbon number range from 8 to 20 and are predominantly of linear carbon structure.

59. The process of claim 58, wherein the alkanols are contacted and reacted with between about 1 and 15 moles of ethylene oxide per mole of alkanol.

60. The process of claim 59, wherein the alkanols are contacted and reacted with between about 2 and 12 moles of ethylene oxide per mole of alkanol.

61. The process of claim 60, wherein the barium phosphate is present in an amount between about 0.5 and 2 percent by weight, calculated on the weight of the alkanols.

62. A process for the preparation of ethylene oxide adducts of secondary mono-hydric alkanols having carbon numbers in the range from 6 to 24, inclusive, which comprises contacting and reacting gaseous ethylene oxide with one or a mixture of said alkanols, in the presence of a catalytically-effective amount of barium phosphate, calculated on the weight of the said alkanols.

63. The process of claim 62, wherein the alkanols are in the carbon number range from 8 to 20 and are predominantly of linear carbon structure.

64. The process of claim 63, wherein the alkanols are contacted and reacted with between about 2 and 12 moles of ethylene oxide per mole of alkanol.

65. The process of claim 64, wherein the alkanols are in an agitated liquid phase containing no mole than about 200 ppm water, and having a temperature in the range from about 130° to 190° C.

66. The process of claim 65, wherein the barium phosphate is present in an amount between about 0.2 and 5 percent by weight, calculated on the weight of the alkanols.

* * * * *